United States Patent [19]

Ollinger

[11] 4,059,697
[45] Nov. 22, 1977

[54] N-(SUBSTITUTED)AMINOCARBONYL O,S-DIALKYL PHOSPHORAMIDO(DI)THIOATES AND METHOD OF CONTROLLING ARTHROPODS

[75] Inventor: Janet Ollinger, North Wales, Pa.

[73] Assignee: Rohm and Haas Company, Philadelphia, Pa.

[21] Appl. No.: 662,746

[22] Filed: Mar. 1, 1976

[51] Int. Cl.² .......................... A01N 9/36; C07F 9/24
[52] U.S. Cl. ................................ 424/211; 260/938; 260/968; 260/984
[58] Field of Search ........................ 260/938; 424/211

[56] References Cited
FOREIGN PATENT DOCUMENTS
216,712   7/1968   U.S.S.R. .............................. 260/938

Primary Examiner—Anton H. Sutto

[57] ABSTRACT

This invention relates to novel phosphoramido(di)thioates of the formula

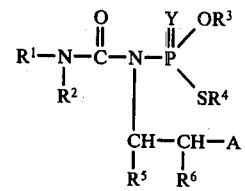

wherein
A is
a. a halogen atom,
b. a cyano group,
c. a ($C_1$-$C_6$) alkoxy group,
d. a ($C_1$-$C_6$) alkylthio group,
e. a ($C_1$-$C_6$) alkylcarbonyloxy group,
f. a phenoxy group, or
g. a phenylthio group;
$R^1$ is
a. a ($C_1$-$C_{12}$) alkyl group,
b. a ($C_3$-$C_8$) cycloalkyl group,
c. an optionally substituted aralkyl group of up to 11 carbon atoms, or
d. an optionally substituted ($C_6$-$C_{10}$) aryl group;
$R^2$ is a hydrogen atom or a ($C_1$-$C_4$) alkyl group when A is a halogen atom, and a hydrogen atom when A is other than a halogen atom;
$R^3$ is a ($C_1$-$C_6$) alkyl group;
$R^4$ is a ($C_1$-$C_6$) alkyl group;

$R^5$ and $R^6$ are independently hydrogen atoms or ($C_1$-$C_4$) alkyl groups; and
Y is an oxygen or sulfur atom;

to compositions containing them, to processes for preparing them, and to methods of utilizing them as arthropodicides.

16 Claims, No Drawings

N-(SUBSTITUTED)AMINOCARBONYL O,S-DIALKYL PHOSPHORAMIDO(DI)THIOATES AND METHOD OF CONTROLLING ARTHROPODS

This invention relates to certain novel phosphoramido(di)thioates, to compositions containing them, to processes for preparing them, and to methods of utilizing them as arthropodicides, especially as insecticides and acaricides.

The novel compounds of this invention can be represented by the formula:

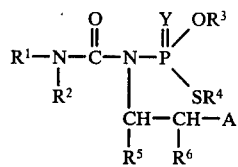

wherein
A is
  a. a halogen atom, preferably chlorine;
  b. a cyano group;
  c. a ($C_1$-$C_6$), preferably ($C_1$-$C_4$), alkoxy group;
  d. a ($C_1$-$C_6$), preferably ($C_1$-$C_4$), alkylthio group;
  e. a ($C_1$-$C_6$), preferably ($C_1$-$C_4$), alkylcarbonyloxy group;
  f. a phenoxy group; or
  g. a phenylthio group;
$R^1$ is
  a. a ($C_1$-$C_{12}$), preferably ($C_1$-$C_8$), alkyl group;
  b. a ($C_3$-$C_8$), preferably ($C_5$-$C_7$), cycloalkyl group;
  c. an optionally substituted aralkyl group of up to 11 carbon atoms, preferably optionally substituted benzyl or phenethyl; or
  d. an optionally substituted ($C_6$-$C_{10}$) aryl, preferably phenyl, group;
$R^2$ is a hydrogen atom or a ($C_1$-$C_4$) alkyl group when A is a halogen atom, and a hydrogen atom when A is other than a halogen atom;
$R^3$ is a ($C_1$-$C_6$), preferably ($C_1$-$C_4$), alkyl group;
$R^4$ is a ($C_1$-$C_6$), preferably ($C_3$-$C_4$), alkyl group;
$R^5$ and $R^6$ are independently hydrogen atoms or ($C_1$-$C_4$) alkyl, preferably methyl, groups, but are preferably hydrogen atoms; and
Y is an oxygen or sulfur, preferably oxygen, atom.

The preferred compounds of this invention demonstrate especially high levels of insecticidal and acaricidal, especially miticidal, activity, and may be represented by the following formula:

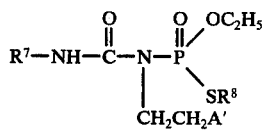

wherein
$R^7$ is
  a. a ($C_1$-$C_8$) alkyl group, preferably a tertoctyl group;
  b. a ($C_5$-$C_7$) cycloalkyl group, preferably a cyclohexyl group;
  c. a benzyl, phenethyl, or phenyl group, preferably a benzyl or phenyl group;
  d. a benzyl, phenethyl, or phenyl group, preferably a phenyl group, substituted with from one to three, preferably with from one to two,
    1. ($C_1$-$C_4$) alkyl, preferably methyl, groups;
    2. ($C_1$-$C_4$) alkoxy, preferably methoxy, groups;
    3. ($C_1$-$C_4$) alkylthio, preferably methylthio, groups;
    4. phenoxy groups;
    5. cyano groups;
    6. nitro groups; or
    7. halogen atoms, preferably bromine or chlorine;
$R^8$ is a ($C_3$-$C_4$) alkyl group, preferably a n-propyl group, an isobutyl group, or a sec-butyl group; and
A' is a halogen atom, preferably chlorine, or a phenylthio group.

Among the preferred compounds, the most preferred are those wherein $R^7$ is a phenyl group or a substituted phenyl group.

As used in the specification and claims, the terms optionally substituted aralkyl and optionally substituted aryl refer to aralkyl groups, e.g. benzyl, phenethyl, naphthylmethylene, etc., and aryl groups, e.g. phenyl and naphthyl, which may be unsubstituted or substituted with up to five, but preferably with up to three, substituents.

Suitable substituents include, for example, ($C_1$-$C_6$) alkyl, preferably ($C_1$-$C_3$) alkyl; ($C_3$-$C_7$) alkenyl, preferably ($C_3$-$C_5$) alkenyl; ($C_1$-$C_6$) alkoxy, preferably ($C_1$-$C_3$) alkoxy; ($C_1$-$C_6$) alkylthio, preferably ($C_1$-$C_3$) alkylthio; ($C_1$-$C_6$) alkylsulfinyl, preferably ($C_1$-$C_3$) alkylsulfinyl; ($C_1$-$C_6$) alkylsulfonyl, preferably ($C_1$-$C_3$) alkylsulfonyl; ($C_1$-$C_6$) alkylcarbonyl, preferably ($C_1$-$C_3$) alkylcarbonyl; di-($C_1$-$C_3$) alkylamino, preferably dimethylamino; ($C_1$-$C_3$) alkylcarbonylamino, preferably methylcarbonylamino; ($C_6$-$C_{10}$) aryl, preferably phenyl; ($C_6$-$C_{10}$) aryloxy, preferably phenoxy; ($C_6$-$C_{10}$) arylthio, preferably phenylthio; cyano; nitro; halogen; halomethyl, preferably trifluoromethyl; and the like. The preferred substituents are ($C_1$-$C_3$) alkyl; ($C_1$-$C_3$) alkoxy; ($C_1$-$C_3$) alkylthio; halogen, especially bromine or chlorine; cyano; nitro; and phenoxy.

The terms alkyl, alkoxy, alkylthio, alkylsulfinyl, alkylsulfonyl, alkylcarbonyloxy, alkylcarbonyl, dialkylamino, alkylcarbonylamino and aralkyl are intended to include branched chain as well as straight chain groups.

Typical examples of compounds within the scope of this invention include the following:

N-(2-chloroethyl) O-ethyl N-methylaminocarbonyl S-propyl phosphoramidothioate or phosphoramidodithioate N-butylaminocarbonyl N-(2-chloroethyl) O-ethyl S-(1-methylpropyl) phosphoramidothioate or phosphoramidodithioate N-(2-chloroethyl) N-dodecylaminocarbonyl O-ethyl S-(2-methylpropyl) phosphoramidothioate or phosphoramidodithioate N-(2-cyanoethyl) N-cyclohexylaminocarbonyl O-ethyl S-propyl phosphoramidothioate or phosphoramidodithioate N-(2-chloroethyl) N-cyclopentylaminocarbonyl O-ethyl S-propyl phosphoramidothioate or phosphoramidodithioate N-benzylaminocarbonyl O-ethyl N-(2-methoxyethyl) S-propyl phosphoramidothioate or phosphoramidodithioate N-(2-chloroethyl) N-(4-chloro-2-methylbenzyl)aminocarbonyl O-ethyl S-propyl phosphoramidothioate or phosphoramidodithioate N-(2-chloroethyl) O-ethyl N-phenethylaminocarbonyl S-propyl phosphoramidothioate or phosphoramidodithioate N-(2-chloroethyl) N-(4-chlorophenethyl)aminocarbonyl O-ethyl S-propyl phosphoramidothioate or phosphoramidodithioate N-(2-chloroethyl) O-ethyl N-(2-naphthylmethylene)aminocrbonyl S-propyl phosphoramidothioate or phosphoramidodithioate O-ethyl N-(2-methylcarbonyloxyethyl) N-phenylaminocarbonyl S-propyl phosphoramidothioate or phosphoramidodithioate O-butyl N-phenylaminocarbonyl N-(2-phenylthioethyl) S-propyl phosphoramidothioate or phosphoramidodithioate O-ethyl N-(2-methylthioethyl) N-phenylaminocarbonyl S-propyl phosphoramidothioate or phosphoramidodithioate N-(2-bromoethyl) N-(4-bromo-2-chlorophenyl)aminocarbonyl O-ethyl S-(2-methylpropyl) phosphoramidothioate or phosphoramidodithioate N-(2,4-dichlorophenyl)aminocarbonyl O-methyl S-(1-methylpropyl) N-(2-phenoxyethyl) phosphoramidothioate or phosphoramidodithioate N-(4-bromo-2-methylphenyl)aminocarbonyl S-butyl N-(2-chloroethyl) O-ethyl phosphoramidothioate or phosphoramidodithioate O-ethyl N-(2-phenylthioethyl) S-propyl N-(2,4,6-trichlorophenyl)aminocarbonyl phosphoramidothioate or phosphoramidodithioate O-ethyl S-(2-fluoroethyl) N-(3-methylthiophenyl)aminocarbonyl S-pentyl phosphoramidothioate or phosphoramidodithioate N-(2-chloroethyl) O-ethyl S-(2-methylpropyl) N-(4-phenoxyphenyl)aminocarbonyl phosphoramidothioate or phosphoramidodithioate N-(4-butoxyphenyl)aminocarbonyl O-methylethyl N-(2-phenylthioethyl) S-propyl phosphoramidothioate or phosphoramidodithioate N-(2-chloroethyl) O-ethyl S-hexyl N-(3-methyl-4-nitrophenyl) aminocarbonyl phosphoramidothioate or phosphoramidodithioate N-(2-chloroethyl) O-ethyl N-(4-dimethylaminophenyl)aminocarbonyl S-propyl phosphoramidothioate or phosphoramidodithioate N-(2-chloroethyl) S-(1-methylpropyl) O-propyl N-(4-propylsulfonylphenyl)aminocarbonyl phosphoramidothioate or phosphoramidodithioate N-(2-chloroethyl) O-ethyl S-propyl N-(2-biphenyl)aminocarbonyl phosphoramidothioate or phosphoramidodithioate N-(2-chloroethyl) O-ethyl N-(1-naphthyl)aminocarbonyl S-propyl phosphoramidothioate or phosphoramidodithioate N-(2-chloroethyl) N-(4-chloro-2-methylphenyl)aminocarbonyl O-ethyl S-(1-methylpropyl) phosphoramidothioate or phosphoramidodithioate N-(2-chloroethyl) N-(3,5-ditrifluoromethylphenyl)aminocarbonyl O-ethyl S-propyl phosphoramidothioate or phosphoramidodithioate N-(2-chloroethyl) O-ethyl N-(4-methylsulfinylphenyl)aminocarbonyl S-propyl phosphoramidothioate or phosphoramidodithioate N-(2-chloroethyl) O-ethyl N-(4-methylcarbonylphenyl)aminocarbonyl S-(2-methylpropyl) phosphoramidothioate or phosphoramidodithioate O-ethyl N-(4-chloro-2-methylphenyl)aminocarbonyl S-(2-methylpropyl) N-(2-phenylthioethyl) phosphoramidothioate or phosphoramidodithioate O-ethyl N-(4-methylcarbonylaminophenyl)aminocarbonyl N-(2-phenylthioethyl) S-propyl phosphoramidothioate or phosphoramidodithioate N-(4-chlorophenyl)aminocarbonyl O-ethyl N-(2-phenylthioethyl) S-propyl phosphoramidothioate or phosphoramidodithioate O-ethyl N-(1-methyl-2-phenylthioethyl) N-phenylaminocarbonyl S-propyl phosphoramidothioate or phosphoramidodithioate N-(4-chloro-2-methylphenyl)aminocarbonyl N-(2-chloropropyl) O-ethyl S-(2-methylpropyl) phosphoramidothioate or phosphoramidodithioate N-(2-chloro-1-methylpropyl) N-(2,3,4,5,6-pentachlorophenyl) aminocarbonyl O-ethyl S-(1-methylpropyl) phosphoramidothioate or phosphoramidodithioate N-[(N'-butyl, N'-phenyl)aminocarbonyl)] N-(2-chloroethyl) O-ethyl S-propyl phosphoramidothioate or phosphoramidodithioate and the like.

The phosphoramido(di)thioates of Formula I can be prepared by various processes. The present invention provides two such processes, each of which represents a novel synthesis. The first process involves the preparation of compounds of the formula:

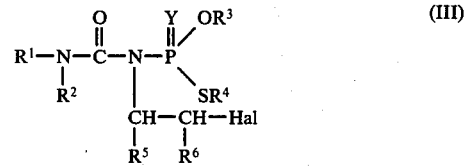

(III)

wherein Hal is a halogen atom, preferably chlorine, $R^2$ is a hydrogen atom or a ($C_1$–$C_4$) alkyl group, and $R^1$, $R^3$, $R^4$, $R^5$, $R^6$ and Y are as defined for Formula I. This synthesis involves reacting an appropriately substituted oxazolidine with a thiophosphoryl or thiolthiophosphoryl halide to produce the intermediate halide salt of the oxazolidine, which then rearranges to provide the appropriate phosphoramido(di)thioate.

The reaction can be represented by the following equation:

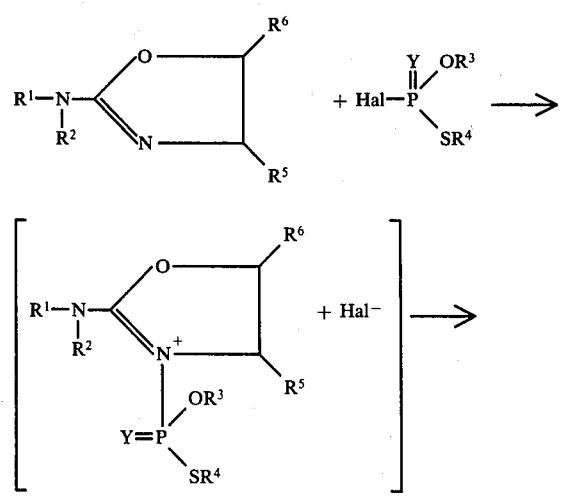

-continued

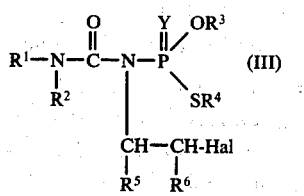

The reaction is advantageously carried out in the presence of an inert organic solvent or mixture of inert organic solvents. Suitable solvents include for example, acetonitrile; dimethylformamide; sulfolane; ether solvents such as tetrahydrofuran, dioxane, diethyl ether and dimethoxy ethane; aliphatic hydrocarbons such as pentane, hexane, heptane, and octane; aromatic hydrocarbons such as benzene and toluene; and ketones such as acetone, methyl ethyl ketone, and the like. The ether solvents are preferred, tetrahydrofuran being the most preferred solvent.

The reaction is generally carried out at a temperature range of about $-20°$ C. to about $100°$ C., and preferably at about $0°$ C. to about $50°$ C. A substantially equimolar ratio of reactants is preferred, but an excess of either reactant can be employed.

The desired product can be separated from the reaction mixture by column chromatography or other conventional techniques.

The second novel process of this invention concerns the preparation of compounds of the formula:

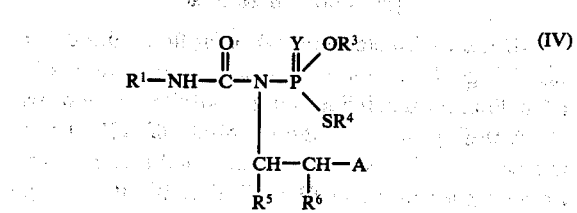

wherein A, $R^1$, $R^3$, $R^4$, $R^5$, $R^6$, and Y are as defined for Formula I. This synthesis involves reacting a phosphorylated oxazolidine with an appropriate acid, alcohol or mercaptan.

The reaction can be represented by the following equation:

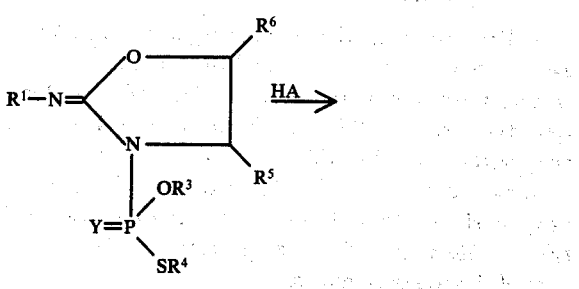

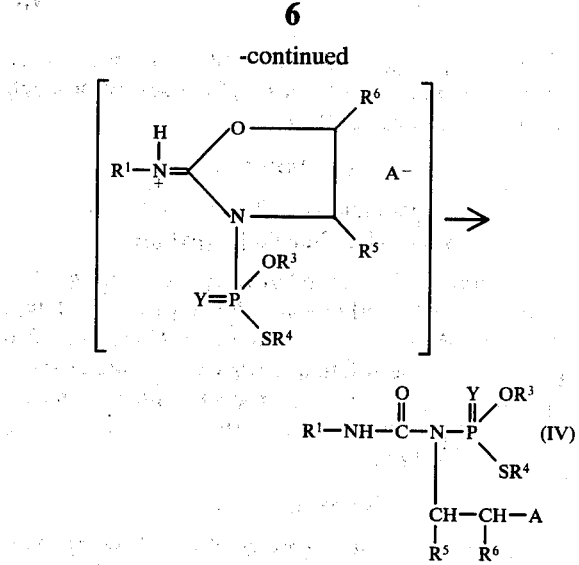

Reaction conditions, including choice of solvents, temperature, molar ratios, and the like, correspond to the conditions described above for the preparation of compounds of Formula III.

With the exception of the phosphorylated oxazolidines, the starting materials used in the preparation of the compounds of this invention are known compounds or are readily prepared by methods available to those skilled in the art.

The phosphorylated oxazolidine starting materials and process for preparing them are the subjects of separate inventions which are disclosed and claimed respectively in U.S. patent applications, Ser. No. 644,288, filed by H. O. Byaer and J. Ollinger, and Ser. No. 644,285, filed by J. Ollinger on Dec. 24, 1975, which applications are assigned to a common assignee and are incorporated herein by reference.

The process for preparing the phosphorylated oxazolidines involves reacting the appropriate oxazolidine with a thiophosphoryl or thiolthiophosphoryl halide in the presence of a strong base, at a temperature range of about $-20°$ C. to about $50°$ C., and preferably in the presence of an inert organic solvent.

By way of demonstration, the following preparations are offered to illustrate this invention and are not to be construed as limitations thereof. Examples 1 to 19 are representative preparations of starting materials used in the synthesis of compounds of this invention. Examples 20 to 45 are representative preparations of compounds of this invention.

EXAMPLE 1

Preparation of N-methyl-4-chloro-2-methylaniline

A mixture of sulfuric acid, 1.1 g. (0.01 mole), trimethyl orthoformate, 45 g. (0.42 mole), and 4-chloro-2-methylaniline, 40 g. (0.28 mole) is heated at $100°$ C. until methanol distillation almost ceases. The reaction is then heated at $175°$ C. for 30 minutes and the residue is fractionally distilled in vacuo. The fraction distillation at $124°/1$ mm. is 16 g. (31% of theory) of the intermediate formanilide.

The formanilide and 41 ml. of 10% hydrochloric acid are heated at reflux for one hour, cooled and basified with 15% sodium hydroxide. The lower amine layer is separated and the aqueous layer is extracted with 50 ml. of ether. The combined organic solutions are dried with magnesium sulfate, filtered and then concentrated by

EXAMPLE 2

Preparation of N-(2-chloroethyl) N'-(4-chloro2-methylphenyl)urea

A solution of 2-chloroethyl isocyanate, 28.3 g. (0.27 mole) in 100 ml. of ether is added dropwise to a solution of 4-chloro-2-methylaniline, 38.0 g. (0.27 mole), in 500 ml. of ether. The solution is stirred 16 hours at room temperature, and the solid product is filtered and air dried, giving 47.2 g. (71% of theory) of the desired product, m.p. 190°.

EXAMPLES 3 to 10

The following are representative of compounds which can be prepared using a procedure similar to that described for Example 2.

N-(2-chloroethyl)-N'-phenylurea, m.p. 121-122° C.
N-(2-chloroethyl)-N'-(4-chlorophenyl)urea, m.p. 159-161° L C.
N-(2-chloroethyl)-N'-(4-methoxyphenyl)urea, m.p. 148° C.
N-(2-chloroethyl)-N'-(4-cyanophenyl)urea, m.p. 141.5-142° C.
N-(2-chloroethyl)-N'-(4-methylthiophenyl)urea, m.p. 121.5-122° C.
N-(2-chloroethyl)-N'-(2,4-dichlorophenyl)urea, m.p. 179.5-181° C.
N-(2-chloroethyl)-N'-(4-phenoxyphenyl)urea, m.p. 145° C.
N-(2-chloroethyl)-N'-(4-chloro-2-methylphenyl)-N'-methylurea, m.p. 189° C.

EXAMPLE 11

Preparation of 2-(4-methylthiophenylimino) oxazolidine

A suspension of 15 g. (0.06 mole) of N-(2-chloroethyl)-N'-(4-methylthiophenyl)urea and 3 drops of Triton ® X-100 surfactant, a polyoxyethylated derivative of alkylphenol, in 500 ml. of water is refluxed in 1¼ hours. The solution is cooled to room temperature and filtered. The filtrate is basified with ammonium hydroxide in order to precipitate the desired product. The product is filtered, washed with water, and air dried to yield 9 g. (70% of theory) of the desired oxazolidine, m.p. 124°-126° C.

EXAMPLES 12 to 18

In a similar manner, the following oxazolidines are likewise readily prepared.
2-(3-methylphenylimino) oxazolidine, m.p. 106°-112° C.
2-(3-chlorophenylimino) oxazolidine, m.p. 83°-87° C.
2-(4-chloro-2-methylphenylimino) oxazolidine, m.p. 111°-112° C.
2-(2,4-dichlorophenylimino) oxazolidine, m.p. 135° C.
2-(4-cyanophenylimino) oxazolidine, m.p. 131°-134° C.
2-(4-phenoxyphenylimino) oxazolidine, m.p. 95°-100° C.
2-(4-chloro-2-methyl-N-methylphenylamino) oxazolidine, oil

EXAMPLE 19

Preparation of 3-(O-ethyl S-propylthiophosphoryl)-2-phenylimino oxazolidine

O-Ethyl S-propyl phosphorochloridothioate, 2.7 g. (0.013 mole), is added to an ice-cooled solution of 2-phenylimino oxazolidine, 2.0 g. (0.013 mole), and triethylamine, 1.6 g. (0.015 mole), in 30 ml. of tetrahydrofuran (THF). The solution is stirred for one hour at ice bath temperature and then filtered. The solvent is evaporated by vacuum stripping, leaving a residue of 4.2 g. A 2.5 g. portion of residue is chromatographed on 50 g. of 60-200 mesh silica gel. Elution with 400 ml. of ether gives 1.0 g. (40% of theory) of the desired product.

EXAMPLE 20

Preparation of N-(2-chloroethyl) O-ethyl N-phenylaminocarbonyl S-propyl phosphoramidothioate Gaseous hydrochloric acid is bubbled into a solution of 2.0 g. (0.00628 mole) of 3-(O-ethyl S-propylthiophosphoryl)-2-phenylimino oxazolidine, in 30 ml. of dry THF. After ten minutes, triethylamine is added to react with the excess hydrochloric acid. The solution is diluted with 50 ml. of THF, filtered, and the solvent removed by vacuum stripping, leaving a residue of 2.3 g. Chromatography on 40 g. of 60-200 mesh silica gel (eluting with 250 ml. of 10% ether in benzene) gives 1.9 g. (86%) of the desired product.

EXAMPLE 21

Preparation of N-(2-chloroethyl) O-ethyl S-(1-methylpropyl) N-phenylaminocarbonyl phosphoramidothioate O-Ethyl S-(1-methylpropyl) phosphorochloridothioate, 2.3 g. (0.01 mole), is added to a solution of 2-phenylimino oxazolidine, 1.6 g. (0.015 mole), and pyridine*, 0.87 g. (0.011 mole), in 15 ml. of THF at room temperature. The solution is stirred for one hour at room temperature and filtered. The filtrate is evaporated by vacuum stripping, leaving 3.6 g. of an oil. Chromatography on 150 g. of 60-200 mesh silica gel (elution with 800 ml. of 10% ether in benzene) gives 1.9 g. (49% of theory) of the desired product as an oil.

*unnecessary reagent in this preparation.

EXAMPLE 28

Preparation of N-(2-chloroethyl) N-(4-chlorophenyl)aminocarbonyl O-ethyl S-(1-methylpropyl) phosphoramidothioate O-Ethyl S-(1-methylpropyl) phosphorochloridothioate, 2.2 g. (0.01 mole), is added to a solution of 2-(4-chlorophenylimino) oxazolidine, 2.0 g. (0.01 mole), and pyridine* 0.81 g. (0.011 mole), in 15 ml. of THF at room temperature and filtered. The filtrate is evaporated by vacuum stripping, leaving 3.5 g. of an oil. Chromatography on 150 g. of 60-200 mesh silica gel (elution with 800 ml. of 10% ether in benzene) gives 1.3 g. (31% of theory) of the desired product.

*unnecessary reagent in this preparation.

EXAMPLE 33

Preparation of N-(2-chloroethyl) O-ethyl N-(4-methylthiophenyl)aminocarbonyl S-propyl phosphoramidothioate To a solution of 2.1 g. (0.01 mole) of 2-(4-methylthiophenylimino) oxazolidine, in 25 ml. of THF at room temperature is added 2.0 g. (0.01 mole) of O-ethyl S-propyl phosphorochloridothioate. After stirring at room temperature for one hour, the solution is diluted with 100 ml of ether and filtered. The filtrate is evaporated by vacuum stripping leaving 3.1 g. of reddish oil which is chromatographed on 100 g. of 60–200 mesh silica gel. Elution with 750 ml. of 10% ether in benzene gives 1.5 g. (37% of theory) of the desired product.

EXAMPLE 40

Preparation of N-(2-chloroethyl) N-(4-chloro2-methylphenyl)aminocarbonyl O-ethyl S-(2-methylpropyl) phosphoramidothioate O-Ethyl S-(2-methylpropyl) phosphorochloridothioate, 4.55 g. (0.02 mole), is added to a solution of 2-(4-chloro2-methylphenylimino) oxazolidine, 4.0 g. (0.019 mole), and pyridine*, 1.6 g. (0.021 mole), in 50 ml. of THF at room temperature. The solution is stirred one hour at room temperature and filtered. The filtrate is evaporated by vacuum stripping, leaving 7.8 g. of an oil. Chromatography on 100 g. of 60–200 mesh silica gel (elution with 600 ml. of 10% ether in benzene) gives 2.8 g. (35% of theory) of the desired product as an oil.
*unnecessary reagent in this preparation.

EXAMPLE 42

Preparation of N-(2-chloroethyl) O-ethyl b 1,1,3,3-tetramethylbutylaminocarbonyl S-propyl phosphoramidothioate A solution of 2-(1,1,3,3-tetramethylbutyl)imino oxazolidine, 2.1 g. (0.010 mole), and O-ethyl S-propyl phosphorochloridothioate, 2.02 g. (0.010 mole), in 25 ml. of THF is stirred for one hour at 25° C. The THF is evaporated by vacuum stripping leaving 4.1 g. of yellow oil. Chromatography on 75 g. of 60–200 mesh silica gel (elution with 500 ml. of 10% ether in benzene) gives 1.52 g. (37% of theory) of the desired product as an oil.

EXAMPLE 43

Preparation of N-(2-chloroethyl) N-cyclohexylaminocarbonyl O-ethyl S-propyl phosphoramidothioate A solution of 2-cyclohexylimino oxazolidine, 2.5 g. (0.0149 mole), and O-ethyl S-propyl phosphoramidothioate, 3.0 g. (0.0149 mole), in 30 ml. of THF is stirred for one hour at room temperature. The solvent is evaporated by vacuum stripping, leaving 5.6 g. of oil. Chromatography on 110 g. of 60–200 mesh silica gel (elution with 400 ml. of 10% ether in benzene) gives 4.3 g. (78% of theory) of the desired product as a clear oil.

EXAMPLE 44

Preparation of N-benzylaminocarbonyl N-(2-chloroethyl) O-ethyl S-propyl phosphoramidothioate A solution of 2-(benzylimino)oxazolidine, 1.0 g. (0.0568 mole) and O-Ethyl S-propyl phosphorochloridothionate, 1.15 g. (0.0568 mole) in 15 ml. of THF is stirred for one hour at room temperature. The THF is evaporated by vacuum stripping, leaving 2.3 g. of light yellow oil. Chromatography on 30 g. of 60–200 mesh silica gel (elution with 300 ml. of 10% ether in benzene, discarding the first 100 ml.) gives 1.6 g. (74% of theory) of product as an oil.

EXAMPLE 45

Preparation of N-(4-chloro-2-methylphenyl)aminocarbonyl O-ethyl N-(2-phenylthioethyl) S-propyl phosphoramidothioate A solution of thiophenol, 0.33 g. (0.003 mole), and 2-(4-chloro-2-methylphenylimino)-3-(O-ethyl S-propylthiophosphoryl) oxazolidine, 1.0 g. (0.00266 mole), in 15 ml. of THF is stirred 8 days at room tempertaure and then refluxed for three hours. The solvent is removed by vacuum stripping, leaving 1.4 g. of yellow oil. Chromatography on 50 g. of 60–200 mesh silica gel (elution with 400 ml. of 10% ether in benzene) gives 0.1 g (8%) of the desired product. nmr:

9.7 (s, 1H), 7.92 (m, 1H), 7.25 (m, 7H), 4.22 (m, 2H), 3.65 (m, 2H), 3.3 (m, 2H), 2.85 (d of t, 2H, J=7 Hz), 2.28 (s, 3H), 1.72 (sextet, 2H, J=7 Hz), 1.33 (t, 3H, J=7 Hz), 0.98 (t, 3H, J=7 Hz).

TABLE I

ELEMENTAL ANALYSIS DATA

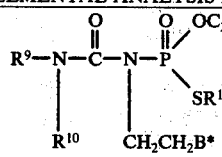

CH$_2$CH$_2$B*

| Example No. | R$^9$ | R$^{10}$ | R$^{11}$ | ANALYSIS CALCULATED (FOUND) | | | |
|---|---|---|---|---|---|---|---|
| | | | | C | H | N | P |
| 20 | C$_6$H$_5$ | H | C$_3$H$_7$ | 46.0 (45.6) | 6.12 (6.25) | 7.58 (7.31) | 8.49 (8.12) |
| 21 | C$_6$H$_5$ | H | C$_4$H$_9$-sec | 47.5 (47.7) | 6.49 (6.84) | 7.60 (7.69) | 8.40 (7.84) |
| 22 | 2-Cl—C$_6$H$_4$ | H | C$_3$H$_7$ | 42.0 (42.3) | 5.34 (5.34) | 7.12 (7.16) | 7.89 (7.39) |
| 23 | 3-Cl—C$_6$H$_4$ | H | C$_3$H$_7$ | 42.0 (41.7) | 5.34 (5.19) | 7.12 (6.85) | 7.89 (7.64) |
| 24 | 4-Cl—C$_6$H$_4$ | H | C$_3$H$_7$ | 42.0 (41.6) | 5.34 (5.23) | 7.12 (6.87) | 7.89 (7.95) |
| 25 | 2-CH$_3$—C$_6$H$_4$ | H | C$_3$H$_7$ | 47.4 (47.2) | 6.33 (6.30) | 7.40 (7.23) | 8.18 (8.21) |
| 26 | 3-CH$_3$—C$_6$H$_4$ | H | C$_3$H$_7$ | 47.4 (46.9) | 6.33 (6.29) | 7.40 (7.21) | 8.18 (8.05) |
| 27 | 4-CH$_3$C$_6$H$_4$ | H | C$_3$H$_7$ | 47.4 (47.0) | 6.33 (6.32) | 7.40 (7.26) | 8.18 (8.25) |
| 28 | 4-Cl—C$_6$H$_4$ | H | C$_4$H$_9$-sec | 43.6 (43.6) | 5.57 (5.75) | 6.77 (6.73) | 7.51 (6.87) |
| 29 | 4-Br—C$_6$H$_4$ | H | C$_3$H$_7$ | 37.8 (37.6) | 4.73 (4.74) | 6.33 (6.19) | 7.00 (6.87) |
| 30 | 4-CN—C$_6$H$_4$ | H | C$_3$H$_7$ | 46.2 (46.1) | 5.37 (5.59) | 10.8 (10.9) | 7.95 (7.88) |
| 31 | 4-NO$_2$—C$_6$H$_4$ | H | C$_3$H$_7$ | 41.0 (40.8) | 5.13 (5.21) | 10.3 (10.4) | 7.57 (7.38) |
| 32 | 4-CH$_3$O—C$_6$H$_4$ | H | C$_3$H$_7$ | 45.5 (46.8) | 6.09 (6.39) | 7.12 (7.03) | 7.85 (7.92) |
| 33 | 4-CH$_3$S—C$_6$H$_4$ | H | C$_3$H$_7$ | 43.8 (43.6) | 5.85 (6.10) | 6.82 (6.74) | 7.55 (7.55) |

TABLE I-continued
ELEMENTAL ANALYSIS DATA

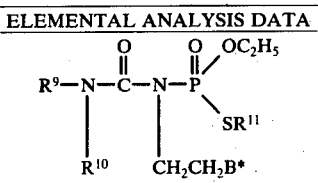

*B is -Cl except in Example 45 wherein B is —SC$_6$H$_5$.

| Example No. | R$^9$ | R$^{10}$ | R$^{11}$ | C | H | N | P |
|---|---|---|---|---|---|---|---|
| 34 | 4-C$_6$H$_5$O—C$_6$H$_4$ | H | C$_3$H$_7$ | 52.6 (51.9) | 5.71 (5.91) | 6.15 (5.88) | 6.78 (6.76) |
| 35 | 2,4-(CH$_3$)$_2$C$_6$H$_3$ | H | C$_3$H$_7$ | 48.9 (48.5) | 6.62 (7.00) | 7.13 (7.13) | 7.90 (7.74) |
| 36 | 2,4-Cl$_2$—C$_6$H$_3$ | H | C$_3$H$_7$ | 38.8 (39.0) | 4.62 (4.91) | 6.45 (6.35) | 7.15 (7.05) |
| 37 | 3,4-Cl$_2$—C$_6$H$_3$ | H | C$_3$H$_7$ | 38.8 (39.0) | 4.62 (4.81) | 6.45 (6.48) | 7.15 (7.11) |
| 38 | 4-Cl, 2-CH$_3$—C$_6$H$_3$ | H | C$_3$H$_7$ | 43.6 (43.6) | 5.58 (5.76) | 6.77 (6.41) | 7.52 (7.37) |
| 39 | 4-Cl, 2-CH$_3$—C$_6$H$_3$ | CH$_3$ | C$_3$H$_7$ | 44.9 (44.5) | 5.86 (6.05) | 6.47 (6.26) | 7.26 (6.72) |
| 40 | 4-Cl, 2-CH$_3$—C$_6$H$_3$ | H | C$_4$H$_9$-iso | 49.3 (45.2) | 6.08 (5.90) | 7.17 (6.26) | 7.92 (6.72) |
| 41 | 2-CH$_3$—4-NO$_2$—C$_6$H$_3$ | H | C$_3$H$_7$ | 42.5 (41.8) | 5.42 (5.72) | 9.90 (9.69) | 7.31 (7.50) |
| 42 | C$_8$H$_{17}$—t | H | C$_3$H$_7$ | 48.0 (48.1) | 8.50 (9.11) | 7.00 (6.85) | 7.75 (6.85) |
| 43 | C$_6$H$_{11}$-cyclo | H | C$_3$H$_7$ | 45.8 (45.5) | 6.54 (8.03) | 7.63 (7.37) | 8.44 (8.18) |
| 44 | C$_6$H$_5$CH$_2$ | H | C$_3$H$_7$ | 47.5 (46.9) | 6.33 (6.76) | 7.40 (7.25) | 8.19 (9.30) |
| 45 | 4-Cl, 2-CH$_3$—C$_6$H$_3$ | H | C$_3$H$_7$ | — — | — — | — — | — — |

The compounds of this invention are useful for the protection of plants and animals, including man, from the ravages of harmful and annoying pests. These compounds are particularly effective against arthropods (in varying stages of development) and are especially effective against members of the Class Arachnoidea, which includes the Order Acarina, as represented by mites and ticks, and the Order Insecta, the insects. Certain compounds of this invention also possess activity as nematocides.

Initial evaluations are made on the following representative species:

| Code Symbol | Common Name | Latin Name |
|---|---|---|
| TSM | Two-spotted spider mite | *Tetranychus urticae* |
| GPA | Green peach aphid | *Myzus persicae* |
| BB | Mexican bean beetle | *Epilachna varivestis* |
| AW | Southern armyworm | *Spodoptera eridania* |
| HF | House fly | *Musca domestica* |

A test solution containing 600 ppm of test compound can be made by dissolving the test compound in a solvent (acetone:methanol, 1:1), adding surfactant and then water to give an acetone:methanol:water system of 10:10:80. A 1:1 mixture of an alkylarylpolyether-alcohol (commercially available under the trademark Triton X-155) and a modified phthalic glycerol alkyd resin (commercially available under the trademark Triton B-1956) can be utilized at the equivalent of one ounce per gallon of test solution as a surfactant.

For the mite test, infested bean (*Phaseolus limeanus*) leaf discs (1.25 inches in diameter) containing about 50 mites and, for green peach aphid tests, infested broccoli (*Brassica oleracae italica*) leaves or portions thereof containing about 50 aphids, are placed in a Petri dish lid on a moistened piece of cotton. The leaves are then sprayed with the test solution using a rotating turntable. They are held for 24 hours and then the percent kill is determined.

For the bean beetle and armyworm test, detached bean leaves on pieces of moistened filter paper are sprayed as above for the mite test in similar dishes and allowed to dry. One such dish is infested with 10 third instar Mexican bean beetle larvae, while another is infested with 10 third instar southern armyworm larvae. The dishes are covered. After holding for 48 hours, the percent kill is obtained.

For the house fly test, half pint glass canning jars with a screened top are used. The test insects consist of 20 adult houseflies, which are supplied with food in the form of sugar water. The jars containing the insects are sprayed using the turntable. The percent kill is determined after 24 hours.

Table II gives the results of the foregoing biological evaluations.

TABLE II
ARTHROPODICIDAL ACTIVITY
Percent control at 600 ppm.

| Example No. | TSM | GPA | AW | BB | HF |
|---|---|---|---|---|---|
| 20 | 100 | 100 | 100 | 100 | 100 |
| 21 | 100 | 100 | 100 | 100 | 100 |
| 22 | 100 | 100 | 100 | 100 | 100 |
| 23 | 100 | 100 | 100 | 100 | 100 |
| 24 | 100 | 100 | 100 | 100 | 100 |
| 25 | 100 | 100 | 100 | 100 | 60 |
| 26 | 100 | 100 | 100 | 90 | 80 |
| 27 | 100 | 100 | 100 | 100 | 85 |
| 28 | 100 | 100 | 100 | 100 | 100 |
| 29 | 100 | 100 | 100 | 100 | 100 |
| 30 | 100 | 100 | 100 | 100 | 100 |
| 31 | 100 | 100 | 100 | 100 | 100 |
| 32 | 100 | 100 | 100 | 100 | 40 |
| 33 | 100 | 100 | 100 | 100 | 100 |
| 34 | 100 | 100 | 100 | 100 | 100 |
| 35 | 100 | 100 | 100 | 100 | 90 |
| 36 | 100 | 100 | 100 | 100 | 100 |
| 37 | 100 | 100 | 100 | 100 | 100 |
| 38 | 100 | 100 | 100 | 100 | 100 |
| 39 | 100 | 100 | 100 | 100 | 100 |
| 40 | 100 | 100 | 100 | 100 | 100 |
| 41 | 100 | 100 | 100 | 100 | 100 |
| 42 | 100 | 100 | 100 | 100 | 0 |
| 43 | 100 | 100 | 90 | 30 | 0 |
| 44 | 100 | 100 | 100 | 100 | 20 |
| 45 | 100 | 100 | 100 | 100 | 80 |

Generally, control of pests is achieved in accordance with this invention by application of the compounds in pesticidally effective amounts (e.g. arthropodicidally effective amounts) either directly to the pests to be controlled or to the loci to be protected from attack by such pests. For example, food, fiber, forage, forest, and ornamental crops and stored products thereof would represent plant protection loci. Treatment with compounds of this invention of domestic animals, man and their immediate environs similarly constitute representative loci for protection against various annoying ectoparasitic or endoparasitic Acarina (Acari) and Insecta.

Accordingly, compounds of the present invention provide utility as the essential active ingredient of pesticidal compositions suitable for agricultural and sanitary purposes.

The term "control" as employed in the specification and claims of this application is to be construed as any means which adversely affects the existence or growth of a living organism. Such means can comprise a complete killing action, eradication, arresting in growth, inhibition, reduction in number, or any combination thereof.

For use as pesticides, the compounds of this invention can be used as solutions in organic solvents or formulations. For example, they can be formulated as wettable powders, emulsifiable concentrates, dusts, granular formulations or flowable emulsifiable concentrates. In such formulations, the compounds of this invention are present at a concentration of about 0.00001 to about 99%, preferably about 1 to about 95%, and are extended with an agronomically acceptable liquid or solid carrier and, when desired, suitable surfactants are likewise incorporated. Surfactants commonly used in the art can be found in the John W. McCutcheon, Inc. publication "Detergents and Emulsifiers Annual."

The compounds of this invention can be taken up on or mixed with a finely particled solid carrier, as for example, clays, inorganic silicates, carbonates, and silicas. Organic carriers can also be employed. Dust concentrates are commonly made wherein the compounds are present in the range of about 20 to about 80%. For ultimate applications, these concentrates are normally extended with additional solid to give an active ingredient content of from 1 to about 20%. Granular formulations are made using a granular or pelletized form of carrier, such as granular clays, vermiculite, charcoal or corn cobs, and can contain the active ingredient in from about 1 to about 25% by weight.

Wettable powder formulations are made by incorporating the compounds of this invention in an inert, finely divided solid carrier along with a surfactant which can be one or more emulsifying, wetting, dispersing or spreading agents or blend of these. The compounds are usually present in the range of about 10 to about 80% by weight and surfactants from about 0.5 to about 10% by weight.

One convenient method for preparing a solid formulation is to impregnate the compound onto the solid carrier by means of a volatile solvent, such as acetone. In this manner, adjuvants, such as activators, adhesives, plant nutrients, synergists and various surfactants can also be incorporated.

Emulsifiable concentrate formulations can be prepared by dissolving the compounds of this invention in an agronomically acceptable organic solvent and adding a solvent-soluble emulsifying agent. Suitable solvents are usually water-immiscible and can be found in the hydrocarbon, ketone, ester, alcohol and amide groups of organic solvents. Mixtures of solvents are commonly employed. The surfactants useful as emulsifying agents can constitute about 0.5 to about 10% by weight of emulsifiable concentrate and can be anionic, cationic, or non-ionic in character. The concentration of the active ingredients can vary from about 10 to about 80%, preferably in the range of about 25 to about 50%.

For use as pesticidal agents, the compounds of this invention should be applied in an effective amount sufficient to exert the desired pesticidal activity by techniques well known in the art. Usually this will involve the application of the compounds to the loci to be protected or freed of pests in an effective amount when incorporated in an agronomically acceptable carrier. However, in certain situations, it may be desirable and advantageous to apply the compounds directly onto the loci to be protected or freed of pests without the benefit of any substantial amount of carrier. This is a particularly effective method when the physical nature of the toxicants is such as to permit what is known as "low-volume" application, that is, when the compounds are in liquid form or substantially soluble in higher boiling solvents.

The application rate will, of course, vary depending upon the purposes for such application, the compounds being utilized, the frequency of dissemination, and the like.

Many of the above formulations can be utilized on animals for control of parasites.

For use as insecticides and acaricides, dilute sprays can be applied at concentrations of about 0.01 to about 20 pounds of the active compound per 100 gallons of spray. They are usually applied at about 0.1 to about 5 pounds per 100 gallons. In more concentrated sprays, the active ingredient in increased by a factor of about 2 to about 12. With dilute sprays, applications are usually made to the plants until run off is achieved, whereas with more concentrated or low-volume sprays, the materials are applied as mists.

For use as soil insecticides or as nematocides, the compounds of this invention can be applied as a solid formulation, preferably a granular formulation, or as a diluted liquid preparation, by broadcasting, side-dressing, soil incorporation or seed treatment. The compositions can also be added to transplant water or employed as dips or soaks for vegetative parts employed in propagation, such as seeds, tubers, roots, seedling, etc., so as to disinfect and/or provide residual protection from nematodes and soil insects. The application rate can be from about 1 to about 50 pounds per acre. For soil incorporation, the compounds of this invention can be mixed with the soil at a rate of about 2 to about 100 ppm.

The compounds of this invention can be utilized as the sole pesticidal agents or they can be employed in conjunction with other bactericides, fungicides, herbicides, insecticides, acaricides, nematocides and comparable pesticides.

Many variations of this invention are possible without departing from the spirit or scope thereof.

We claim:

1. A compound of the formula:

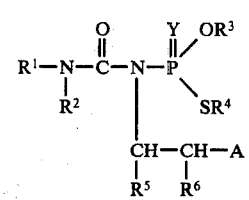

wherein

A is
  a. a halogen atom,
  b. a cyano group,
  c. a $(C_1-C_6)$alkoxy group,
  d. a $(C_1-C_6)$alkylthio group, e. a $(C_1-C_6)$alkylcarbonyloxy group,
f. a phenoxy group, or
g. a phenylthio group;

$R^1$ is
a. a $(C_1-C_{12})$alkyl group,
b. a $(C_3-C_8)$cycloalkyl group,
c. an unsubstituted $(C_7-C_{11})$aralkyl group or a $(C_7-C_{11})$aralkyl group, the aryl portion of which is substituted with up to five substituents selected from the group consisting of $(C_1-C_6)$alkyl, $(C_3-C_7)$alkenyl, $(C_1-C_6)$-alkoxy, $(C_1-C_6)$alkylthio, $(C_1-C_6)$alkylsulfinyl, $(C_1-C_6)$alkylsulfonyl, $(C_1-C_6)$alkylcarbonyl, di$(C_1-C_3)$alkylamino, $(C_1-C_3)$alkylcarbonylamino, $(C_6-C_{10})$aryl, $(C_6-C_{10})$aryloxy, $(C_6-C_{10})$arylthio, cyano, nitro, halogen and halomethyl,
d. an unsubstituted $(C_6-C_{10})$aryl group or a $(C_6-C_{10})$aryl group substituted with up to five substituents selected from the group consisting of $(C_1-C_6)$alkyl, $(C_3-C_7)$alkenyl, $(C_1-C_6)$alkoxy, $(C_1-C_6)$alkylthio, $(C_1-C_6)$alkylsulfinyl, $(C_1-C_6)$alkylsulfonyl, $(C_1-C_6)$alkylcarbonyl, di$(C_1-C_3)$alkylamino, $(C_1-C_3)$alkylcarbonylamino, $(C_6-C_{10})$aryl, $(C_6-C_{10})$-arylthio, cyano, nitro, halogen and halomethyl, $R^2$ is a hydrogen atom or a $(C_1-C_4)$alkyl group when A is a halogen atom, and a hydrogen atom when A is other than a halogen atom;

$R^3$ is a $(C_1-C_6)$ alkyl group;

$R^4$ is a $(C_1-C_6)$alkyl group; $R^5$ and $R^6$ are independently hydrogen atoms or $(C_1-C_4)$alkyl groups; and Y is an oxygen or sulfur atom.

2. A compound according to claim 1 wherein
A is
a. a halogen atom,
b. a cyano group,
c. a $(C_1-C_4)$alkoxy group,
d. a $(C_1-C_4)$alkylthio group,
e. a $(C_1-C_4)$alkylcarbonyloxy group,
f. a phenoxy group, or
g. a phenylthio group;

$R^1$ is
a. a $(C_1-C_8)$alkyl group,
b. a $(C_5-C_7)$cycloalkyl group,
c. a benzyl or phenethyl group, the phenyl portion of which is substituted with up to five substituents selected from the group consisting of $(C_1-C_6)$alkyl, $(C_3-C_7)$alkenyl, $(C_1-C_6)$alkoxy, $(C_1-C_6)$alkylthio, $(C_1-C_6)$alkylsulfinyl, $(C_1-C_6)$alkylsulfonyl, $(C_1-C_6)$alkylcarbonyl, di$(C_1-C_3)$alkylamino, $(C_1-C_3)$alkylcarbonylamino, $(C_6-C_{10})$-aryl, $(C_6-C_{10})$aryloxy, $(C_6-C_{10})$arylthio, cyano, nitro, halogen and halomethyl,
d. a phenyl group or a phenyl group substituted with up to five substituents selected from the group consisting of $(C_1-C_6)$alkyl, $(C_3-C_7)$alkenyl, $(C_1-C_6)$alkoxy, $(C_1-C_6)$alkylthio, $(C_1-C_6)$alkylsulfinyl, $(C_1-C_6)$alkylsulfonyl, $(C_1-C_6)$alkylcarbonyl, di$(C_1-C_3)$alkylamino, $(C_1-C_3)$alkylcarbonylamino, $(C_6-C_{10})$aryl, $(C_6-C_{10})$-aryloxy, $(C_6-C_{10})$arylthio, cyano, nitro, halogen and halomethyl, $R^2$ is a hydrogen atom or a $(C_1-C_4)$alkyl group when A is a halogen atom, and a hydrogen atom when A is other than a halogen atom;

$R^3$ is a $(C_3-C_4)$alkyl group;

$R^4$ is a $(C_3-C_4)$alkyl group;

$R^5$ and $R^6$ are independently hydrogen atoms or methyl groups; and

Y is an oxygen atom.

3. A compound according to claim 2 having the formula:

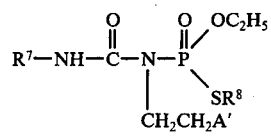

wherein $R^7$ is
a. a $(C_1-C_8)$ alkyl group,
b. a $(C_5-C_7)$ cycloalkyl group,
c. a benzyl, phenethyl or phenyl group,
d. a benzyl, phenethyl or phenyl group, substituted with from one to three
1. $(C_1-C_4)$ alkyl groups,
2. $(C_1-C_4)$ alkoxy groups,
3. $(C_1-C_4)$ alkylthio groups,
4. phenoxy groups,
5. cyano groups,
6. nitro groups, or
7. halogen atoms;

$R^8$ is a $(C_3-C_4)$ alkyl group; and

A' is a chlorine atom or a phenylthio group.

4. A compound according to claim 3 wherein $R^7$ is
a. a tert-octyl group,
b. a cyclohexyl group,
c. a benzyl or phenyl group,
d. a phenyl group substituted with one to two
1. $(C_1-C_4)$ alkyl groups,
2. $(C_1-C_4)$ alkoxy groups,
3. $(C_1-C_4)$ alkylthio groups,
4. phenoxy groups,
5. cyano groups,
6. nitro groups, or
7. halogen atoms.

5. A compound according to claim 4, wherein $R^7$ is a phenyl group or a substituted phenyl group.

6. A compound according to claim 5 having the formula:

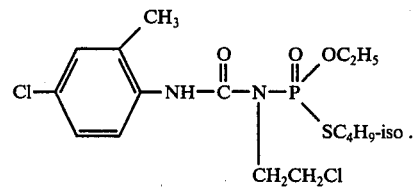

7. A compound according to claim 5 having the formula:

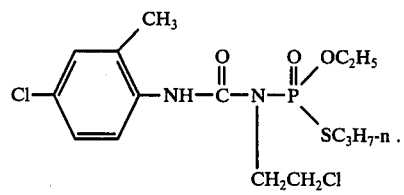

8. A compound according to claim 5 having the formula:

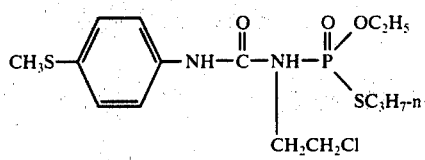

9. A compound according to claim 5 having the formula:

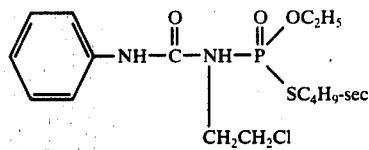

10. A compound according to claim 5 having the formula:

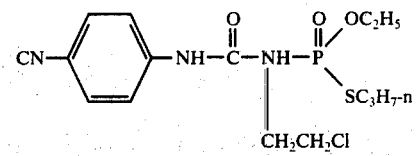

11. An arthropodicidal composition comprising a compound according to claim 1 and an agronomically acceptable carrier.

12. A method of controlling arthropods which comprises applying directly to the arthropods or to the loci to be freed of or protected from attack by such arthropods, an arthropodicidally effective amount of the compound of claim 1.

13. A method of controlling arthropods which comprises applying directly to the arthropod or to the loci to be freed of or protected from attack by such arthropods, an arthropodicidally effective amount of the composition of claim 12.

14. A method according to claim 13 wherein the arthropods are insects.

15. A method according to claim 13 wherein the arthropods are acarids.

16. A method according to claim 15 wherein the acarids are mites.

* * * * *

UNITED STATES PATENT OFFICE
CERTIFICATE OF CORRECTION

Patent No. 4,059,697    Dated November 22, 1977

Inventor(s) Janet Ollinger

It is certified that error appears in the above-identified patent and that said Letters Patent are hereby corrected as shown below:

Claim 8. A compound according to claim 5 having the formula:

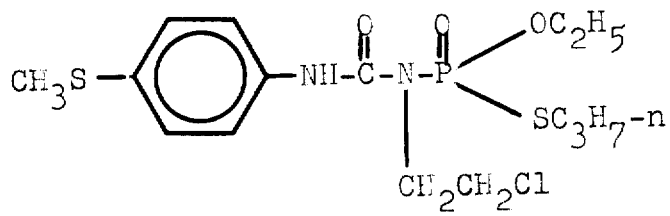

Claim 9. A compound according to claim 5 having the formula:

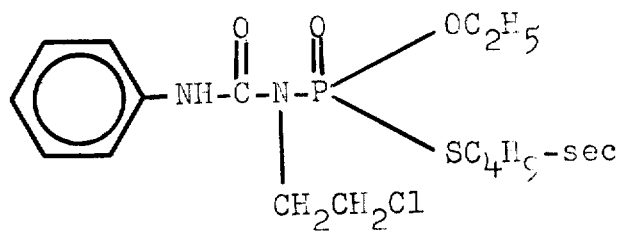

Claim 10. A compound according to claim 5 having the formula:

UNITED STATES PATENT OFFICE
CERTIFICATE OF CORRECTION

Patent No. 4,059,697  Dated November 22, 1977

Inventor(s) Janet Ollinger

It is certified that error appears in the above-identified patent and that said Letters Patent are hereby corrected as shown below:

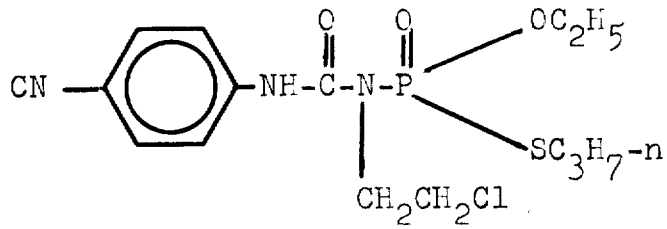

Signed and Sealed this

*Twenty-third* Day of *May 1978*

[SEAL]

*Attest:*

RUTH C. MASON  LUTRELLE F. PARKER
*Attesting Officer*  *Acting Commissioner of Patents and Trademarks*